United States Patent [19]

Instance

[11] Patent Number: 4,744,591

[45] Date of Patent: * May 17, 1988

[54] LABELS AND MANUFACTURE THEREOF

[76] Inventor: David J. Instance, Past Heap Farm, Pembury, Tunbridge Wells, Kent, England

[ * ] Notice: The portion of the term of this patent subsequent to Jun. 3, 2003 has been disclaimed.

[21] Appl. No.: 792,735

[22] Filed: Oct. 29, 1985

[30] Foreign Application Priority Data

Oct. 29, 1984 [GB] United Kingdom ................. 8427291
Feb. 18, 1985 [GB] United Kingdom ................. 8504113

[51] Int. Cl.[4] ...................... B42D 19/00; B42D 15/00; A61F 13/00

[52] U.S. Cl. ....................................... 281/5; 283/1 R; 283/81; 428/40

[58] Field of Search ................. 283/1 R, 48 R, 51, 81; 428/40; 156/52 A, 52 AL; D20/22; 281/5, 1

[56] References Cited

U.S. PATENT DOCUMENTS

| | | | |
|---|---|---|---|
| 4,288,877 | 9/1981 | Klepfer | 428/40 |
| 4,323,608 | 4/1982 | Denny et al. | 283/81 |
| 4,524,095 | 6/1985 | Gockel et al. | 428/40 |
| 4,529,229 | 7/1985 | Glibbery | 283/81 |
| 4,534,582 | 8/1985 | Howard | 283/81 |
| 4,592,572 | 6/1986 | Instance | 428/40 |

*Primary Examiner*—E. R. Kazenske
*Assistant Examiner*—Paul M. Heyrana, Sr.
*Attorney, Agent, or Firm*—Birch, Stewart, Kolasch & Birch

[57] ABSTRACT

A label for affixing to a container comprising a longitudinal strip divided into a series of panels by a plurality of transverse fold lines, the first two panels forming a front cover and a back cover respectively for enveloping the remaining panel or panels of the strip when folded, the transverse fold lines being spaced along the strip so that upon folding of the strip the said remaining panel or panels is or are folded to lie over the back cover and is or are in turn covered by folding of the front cover about the fold line between the front and back covers; a support web to which the said back cover is adhered, the support web being dimensioned so that at least one region thereof extends laterally at least beyond the edge of the back cover which occurs at the fold line between the back cover and the remaining panel or panels; and a layer of pressure-sensitive self-adhesive material which is adhered by the self-adhesive surface thereof over some or all of the front cover panel, the self-adhesive material extending at least beyond the free outer edge of the front cover panel, which free outer edge is opposite the fold line between the front and back cover panels, and the self-adhesive material having at least one portion thereof which can be adhered by the self-adhesive surface thereof to the region, or a respective one of the regions, thereby to secure the front cover panel in a closed condition and can be pulled away from the support web thereby to open the front cover panel and give access to the interior of the folded strip. The invention further provides a method of producing a succession of such labels which are self-adhesive and are carried on a backing of release material.

10 Claims, 5 Drawing Sheets

LABELS AND MANUFACTURE THEREOF

BACKGROUND TO THE INVENTION

The present invention relates to labels, in particular, labels intended to be attached to containers such as boxes, packets, bottles or tins, and to a method of producing a succession of self-adhesive labels carried on a backing of release material.

My British Patent Applications Nos. 8226252, 8305905 and 8415853 disclose so-called "extended text" labels for application to containers.

It is an object of the present invention to provide a label which is an improvement over my previous label in that it has a greater resistance to accidental damage by tearing and soiling, which can occur when the label is to be used in particular labelling applications.

SUMMARY OF THE INVENTION

Accordingly, the present invention provides a label for affixing to a container comprising a longitudinal strip divided into a series of panels by a plurality of transverse fold lines, the first two panels forming a front cover and a back cover respectively for enveloping the remaining panel or panels of the strip when folded, the transverse fold lines being spaced along the strip so that upon folding of the strip the said remaining panel or panels is or are folded to lie over the back cover and is or are in turn covered by folding of the front cover about the fold line between the front and back covers; a support web to which the said back cover is adhered, the support web being dimensioned so that at least one region thereof extends laterally at least beyond the edge of the back cover which occurs at the fold line between the back cove and the remaining panel or panels; and a layer of pressure-sensitive self-adhesive material which is adhered by the self-adhesive surface thereof over some or all of the front cover panel, the self-adhesive material extending at least beyond the free outer edge of the front cover panel, which free outer edge is opposite the fold line between the front and back cover panels, and the self-adhesive material having at least one portion thereof which can be adhered by the self-adhesive surface thereof to the region, or a respective one of the regions, thereby to secure the front cover panel in a closed condition and can be pulled away from the support web thereby to open the front cover panel and give access to the interior of the folded strip.

Preferably, the self-adhesive material extends beyond the said at least one region so that the self-adhesive material is also adhered to a part of the support web which is adjacent to or spaced from said at least one region and an elongate cut or weakened tear line through the self-adhesive material separates the said at least one portion from the remainder of the self-adhesive material which is adhered to the said part of the support web.

According to a preferred arrangement, the cut or weakened tear line extends generally along the free outer edge of the front cover panel except at at least one place at which the cut or weakened tear line extends laterally away from the free outer edge to form the said at least one portion of self-adhesive material.

In addition, the front cover panel may be dimensioned so that the free outer edge extends beyond the area of the support web occupied by the back cover thereby to form an overlapping portion, the overlapping portion being provided with at least one cut-out which exposes the self adhesive surface of the self-adhesive material so as to form the said at least one portion of self-adhesive material.

Preferably, the or each cut-out extends inwardly from the free outer edge to a distance which is greater than the width of the overlapping portion so that the or each portion of self-adhesive material can be adhered both to the support web and to the upper surface of the remaining panel or panels which are exposed by the or each cut-out.

Preferably, the free outer edge of the front cover panel is, apart from the cut outs, a straight line and the cut or weakened tear line is a straight line which is coincident with the straight line of the free outer edge.

Alternatively, the free outer edge of the front cover panel is a straight line and the cut or weakened tear line is substantially a straight line except at the said at least one place.

According to a further preferred arrangement, the front cover panel is dimensioned so that the free outer edge extends beyond the area of the support web occupied by the back cover thereby to form an overlapping portion, the overlapping portion being provided with two or more cut-out holes which are spaced from and generally along the free outer edge of the front cover panel, each cut-out hole exposing the self-adhesive material so as to form two or more of the said portions of self-adhesive material.

Preferably, each cut-out hole is positioned in the front cover panel such that when the front cover panel is folded over the remaining panel or panels each portion of self-adhesive material can be adhered both to the support web and to the upper surface of the remaining panel or panels which are exposed by the respective cut-out holes.

The label desirably comprises a band of the material of the longitudinal strip which is disposed along the free outer edge of the front cover panel when the front cover panel is folded as aforesaid, the band being separated from the front cover panel by the cut or weakened tear line and being adhered to the support web by the remainder of the self-adhesive material which is adhered to the support web.

The present invention further provides a method of producing a succession of self-adhesive labels carried on a backing of release material, the method comprising the steps of:

(a) providing a laminar material comprising a support web coated on its reverse side with a pressure-sensitive adhesive and having a backing of a release material;

(b) applying a layer of adhesive to a succession of particular areas along the length of the support web;

(c) providing a plurality of folded longitudinal strips, each longitudinal strip being divided into a series of panels by a plurality of transverse fold lines, the first two panels forming a front cover and a back cover respectively for enveloping the remaining panel or panels of the strip when folded, the transverse fold lines being spaced along the strip so that upon folding of the strip the said remaining panel or panels is or are folded to lie over the back cover and is or are in turn covered by folding of the front cover about the fold line between the front and back covers;

(d) applying individual folded longitudinal strips to respective successive areas of adhesive so that the back cover of each folded strip covers a respective area of the support web to which adhesive has been applied;

(e) adhering a web of a pressure-sensitive self-adhesive material over the support web and the folded strips;

(f) cutting the web of self-adhesive material and all of the layers of the laminar material other than the backing layer so as to cut a succession of labels on the backing layer, each label having one of the folded strips adhered to a respective part of the support web and each said part of the support web being dimensioned so that at least one region thereof extends laterally at least beyond the edge of the back cover which occurs at the fold line between the back cover and the remaining panel or panels; and (g) cutting, either before, after or simultaneously with cutting step (f), a succession of elongate cuts or weakened tear lines through the self-adhesive material so that in each resultant label the respective cut or weakened tear line separates the self-adhesive material, there being in each resultant label at least one portion of the self-adhesive material which, or each of which, can be adhered by the self-adhesive surface thereof to the region, or a respective one of the regions, of the support web thereby to secure the front cover panel in a closed condition, and can be pulled away from the support web thereby to open the front cover and give access to the interior of the folded strip.

According to a preferred arrangement, the cut or weakened tear line extends generally along the free outer edge of the front cover panel, the free outer edge being opposite the fold line between the front and back cover panels, except at at least one place at which the cut or weakened tear line extends laterally away from the free outer edge to form the said at least one portion of self-adhesive material.

Preferably, the front cover panel is dimensioned so that the free outer edge extends beyond the area of the back cover thereby to form an overlapping portion, the overlapping portion being provided with at least one cut-out which exposes the self-adhesive surface of the self-adhesive material so as to form the said at least one portion of the self-adhesive material.

Preferably, the free outer edge of the front cover panel is, apart from the cut-out or cut-outs, a straight line and the cut or weakened tear line is a straight line which is coincident with the straight line of the free outer edge.

Alternatively, the free outer edge of the front cover panel is a straight line and the cut or weakened tear line is substantially a straight line except at the said at least one place.

According to a further preferred arrangement, the front cover panel is dimensioned so that the free outer edge of the front cover panel, the free outer edge being opposite the fold line between the front and back cover panels, extends beyond the area of the support web occupied by the back cover thereby to form an overlapping portion, the overlapping portion being provided with two or more cut-out holes which are spaced from and generally along the free outer edge of the front cover panel, each cut-out hole exposing the self-adhesive surface of the self-adhesive material so as to form two or more of the said portions of self-adhesive material.

Preferably, each cut-out hole is positioned in the front cover panel such that when the front cover panel is folded over the remaining panel or panels each portion of self-adhesive material can be adhered both to the support web and to the upper surface of the remaining panel or panels which are exposed by the respective cut-out holes.

Preferably, the cut or weakened tear line is also cut through the longitudinal strip to form a band of the material of the longitudinal strip which is disposed along the free outer edge of the front cover panel when the front cover panel is folded over the remaining panel or panels, the band being separated from the front cover panel by the cut or weakened tear line and being adhered to the support web by the self-adhesive material.

Desirably, cutting steps (f) and (g) are carried out simultaneously by a die-cutter.

DESCRIPTION OF THE PREFERRED EMBODIMENTS

Figure 1:
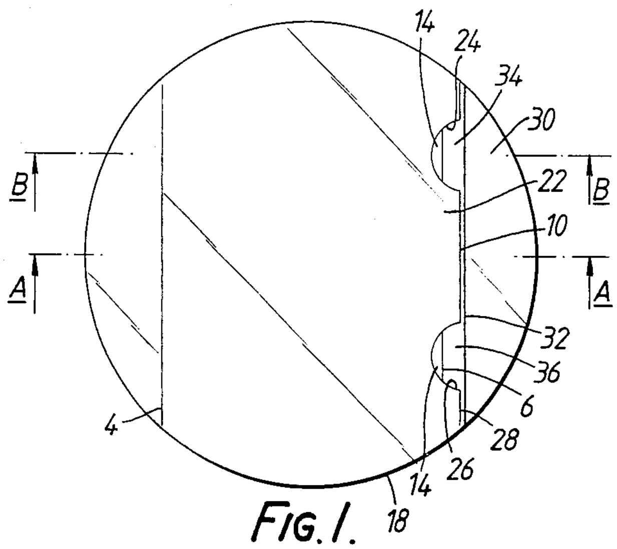
FIG. 1 is a plan view of a label, in a folded condition, in accordance with a first embodiment of the present invention.

In the accompanying drawings, the thickness of the labels is shown greatly exaggerated for the sake of clarity of illustration.

Referring to FIGS. 1 to 5, a label in accordance with the present invention is made from a longitudinal strip 2 of paper which divided by transverse folded lines 4, 6, 8 into four panels 10, 12, 14, 16. The transverse fold lines, 4, 6, 8 need not exist prior to the folding operations used to form the label during its manufacture. The upper surface (in FIGS. 4 and 5) of each of the panels 10, 12, 14, 16 may carry printed information, as can the lowest surface of each of the panels 10, 14 and 16. The lower (or rear) surface of panel 12 is adhered to a support web 18 by a layer of adhesive 20. The upper surface of the support web 18 also carries information on those portions thereof which are not covered by the folded strip 2. The support web 18 may also have an adhesive on its underside suitable for adhering support web 18 together with its associated strip 2 of panels to a container. Preferably the adhesive on the underside of the support web 18 is a pressure-sensitive adhesive which is protected by a release backing material (not shown).

In use, panel 16 is folded about fold line 8 to lie over panel 14. Then panels 14 and 16 are folded about fold line 6 to lie over panel 12. Panel 12 acts as a back cover for the folded label. Thereafter, panel 10 is folded about fold line 4 to lie over panels 14 and 16 and thereby to act as a front cover for the folded label. The fold lines 4, 6, 8 are spaced from one another in such a manner that panels 14 and 16 after folding are both contained within the front and back cover panels 10 and 12. The width of the front cover panel 10 is greater than the width of back cover panel 12 such that the front cover panel 10 has an overlapping portion 22 which in the folded condition extends beyond the right-hand edge of the folded panels 14 and 16, which edge is defined by the fold line 6, and the right-hand edge of the back cover panel 12.

Two cut-outs 24, 26 are provided in the front cover panel 10 at the free outer edge 28 thereof which is opposite to the fold line 4 between the front cover panel 10 and the back cover panel 12. The cut-outs 24, 26 are semi-circular but may, alternatively, be any desired shape. The cut-outs 24, 26 extend inwardly of the panel 10 towards the fold line 4 to a distance which is greater than the width of the overlapping portion 22. Thus when the strip 2 is folded, the cut-outs 24, 26 each expose a surface portion both of the support web 18 and of the folded panel 14, when panel 14 is above panel 16 when the label is folded.

A layer of a see-through, preferably transparent, plastics material 30 covers the folded strip 2 and the front surface of the support web 18 which is not covered by the folded strip 2. The plastics material 30 is self-adhesive and has a coating of a pressure-sensitive adhesive on the underside thereof via which adhesive the plastics material 30 is adhered to the exposed upper surface of the folded strip 2/support web 18 combination. Preferably, the plastics material 30 is an acetate or a polyester film.

When the layer of see-through plastics material is employed, any information which is printed on the front surface of the front cover panel 10 and on the surrounding surfaces of the support web 18 can be seen by a user through the see-through plastics material.

In an alternative arrangement, the layer of plastics material 30 may be opaque and, if desired, itself be printed with information.

Furthermore, instead of a layer of plastics material, a pressure-sensitive self-adhesive paper may be employed in the labels of the invention.

In the illustrated embodiments, the layer of plastics material 30 completely covers the front surface of the label. However, if desired the layer of plastics material 30 may cover only a part of the front surface of the label, provided that the layer of plastics material 30 can adhere the front cover panel 10 to the support web 18 and thereby maintain the folded label in a closed condition.

The layer of plastics material 30 covers and is adhered by its layer of pressure-sensitive adhesive to the surface of the front cover panel 10 and to the front surface of the support web 18 at the side of the folded strip 2. The layer of plastics material 30 is also adhered, due to the presence of cut-outs 24, 26 which expose the self-adhesive surface of the layer of plastics material 30 in those regions, to those surface portions of the folded panel 14 and of the support web 18 which are underneath the cut-outs 24, 26 when the label is folded.

Figure 2:
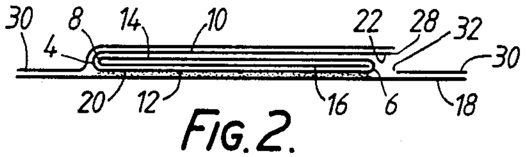
FIG. 2 is a section view, taken along line A—A of the label of FIG. 1.
Figure 3:
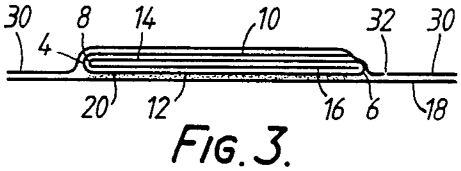
FIG. 3 is a section view, taken along line B—B of the label of FIG. 1.

A cut 32 through the thickness of the layer of plastics material 30 extends generally along the free outer edge 28 of the front cover panel 10. In the illustrated embodiment, the cut 32 is formed as a straight line and so does not coincide with the edges of the cut-outs 24, 26 thereby to provide two tabs 34, 36 of plastics material 30 which are located in the registry with the cut-outs 24, 26. For the sake of clarity of illustration, the cut 32 is shown in FIG. 1 as slightly spaced from the free outer edge 28, whereas in the actual embodiment the cut 32 extends along each portion of the free outer edge 28 which is straight. As is shown more clearly in FIG. 3, the two tabs 34, 36 act so as to adhere the front cover panel 10 to the support web 18 and to the folded panel 14, and thereby to retain the folded label in a closed condition. In the regions along the free outer edge 28 not having the cut-outs 24, 26, as is shown in FIG. 2, free outer edge 28 is not adhered by the layer of plastics material 30 to the adjacent support web 18 since the cut 32 separates the plastics material 30 in those regions. In the resultant labels therefore, it is only the two tabs 34, 36 of plastics material 30 which adhere the front cover panel 10 to the support web 18 and thereby retain the label in a folded condition.

Figure 4:
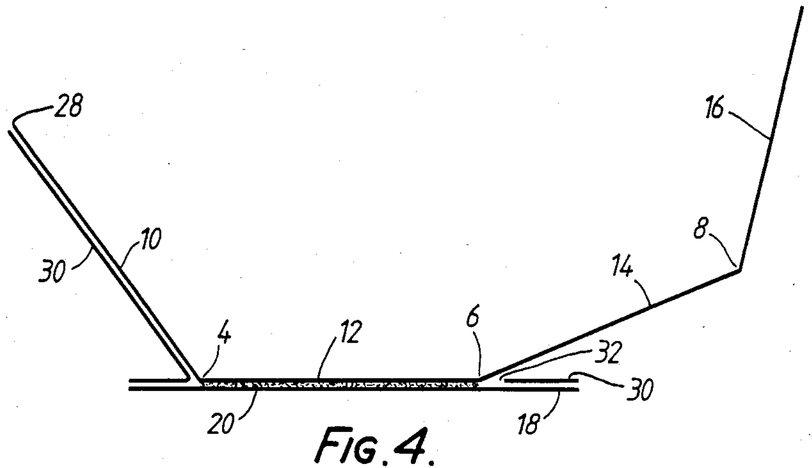
FIG. 4 is a section view, taken along line A—A of the label of FIG. 1 when unfolded.
Figure 5:
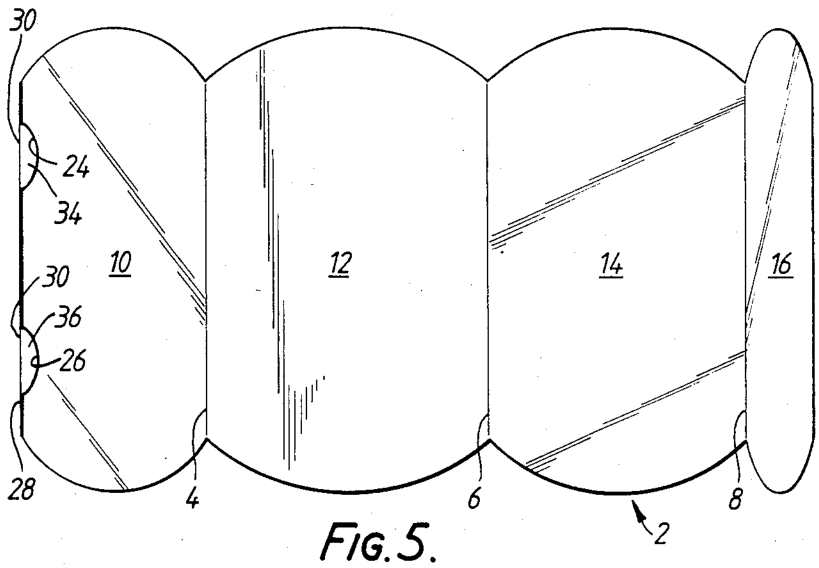
FIG. 5 is a plan view from above of the unfolded label of FIG. 4.

To open the folded label, the two adhered tabs 34, 36 are pulled away from the support web 18 and the folded panel 14 so as to release the front cover panel 10 and allow the label to be opened, to a position such as that shown in FIGS. 4 and 5, where the printed information on the inner surfaces of the panels can be read by a user.

In order to re-close the unfolded label, the folded panels 14, 16 are folded over back cover panel 12 and then front cover panel 10 is folded over the folded panels 14, 16. The front cover panel 10 is re-adhered via tabs 34, 36 of plastics material 30 to the support web 18 and to the folded panel 14.

The pressure-sensitive adhesive which is coated on plastics material 30 is preferably of such a composition so as to allow the front of the panel 10 to be successfully detached from and re-attached to the support web 18 and to the folded panel 14 so that a user can repeatedly open and close the folded label.

In an alternative arrangement of the label of the present invention, the cut-outs 24, 26 may be dimensioned so that they extend inwardly of the front cover panel 10 to a distance which is less than the width of the overlapping portion 22. In that arrangement, when the folded label is closed the tabs 34, 36 of the plastics material 30 are adhered only to the support web 18 and are not adhered to the folded label 14.

Figure 6:
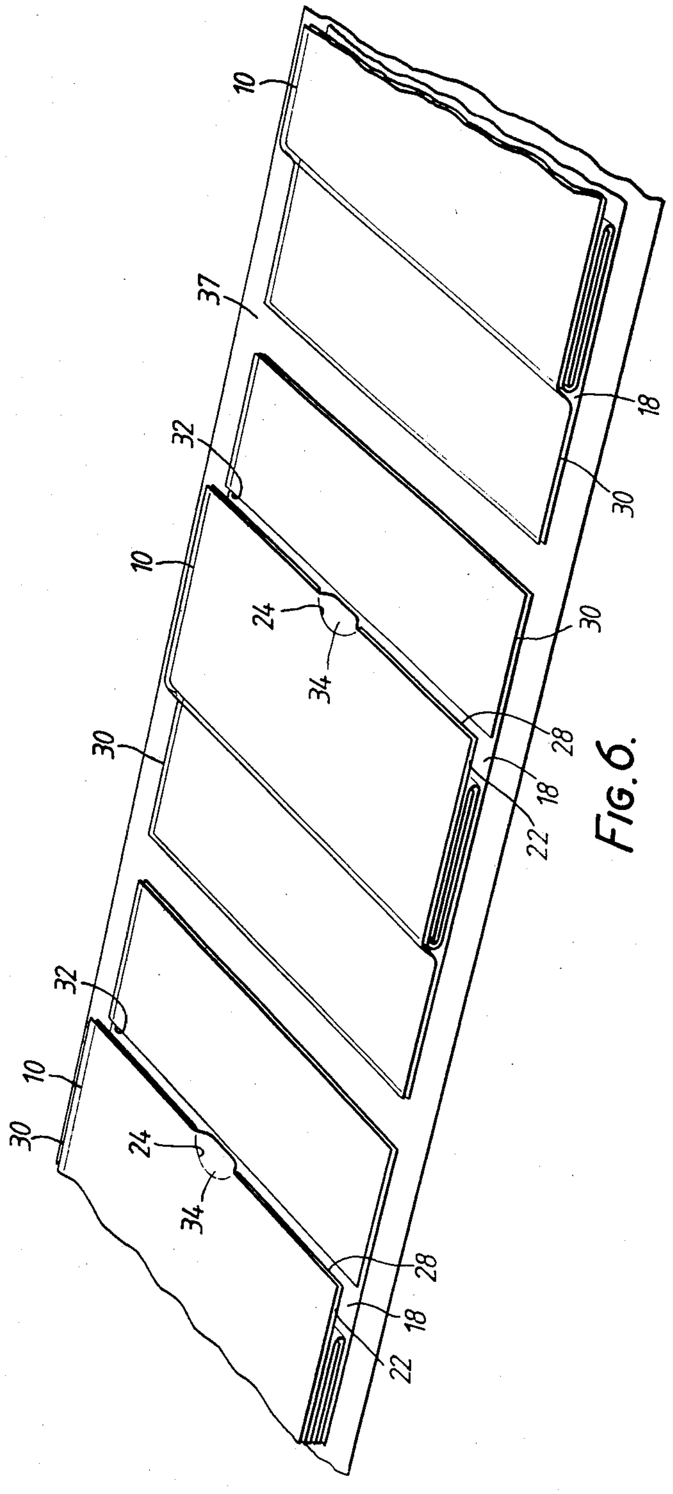
FIG. 6 is a perspective view of a succession of self-adhesive labels in accordance with the second embodiment invention when carried on a length of a release backing material.

Referring to FIG. 6, there is shown a succession of self-adhesive labels carried on a length 37 on release backing material which is preferably a silicone-coated release paper. The labels are rectangular in shape and each label consists of rectangular support web 18 to which is adhered a rectangular folded strip of paper 2. The back surface of each support web 18 is coated with a pressure-sensitive adhesive so that each label is self-adhesive and is releasably carried on the release backing material 37. The strip 2 is folded in a manner similar to that in the embodiment of FIGS. 1 to 5 and the back cover panel 12 of the strip is adhered by a layer of adhesive 20 to the front surface of the support web 18. The layer of 30 of plastics material covers the label and adheres the front cover panel 10 to the support web 18. The front cover panel 10 is provided with only one cut-out 24 at its free outer edge 28 and the cut 32 extends in a straight line along the free outer edge 28 so as to result in a single tab 34 of plastics material 30 which adheres the front cover panel 10 to the support web 18 and maintains the label in a folded condition. The labels shown in FIG. 6 differ from those shown in FIG. 1 to 5 in that in the former labels only one tab 34 of plastics material 30 is present in the label and also the labels are rectangular, rather than circular, in shape. In addition, in the labels of FIG. 6 the width of the overlapping portion 22 of the front cover of panel 10 is greater than the depth of the cut-out 24 such that when the label is folded, the cut-out 24 exposes only a portion of the support web 18 and not a portion of the folded panel 14, as is the case in the embodiment of FIGS. 1 to 5. Thus, when the label is folded, the tab 34 of plastics material 30 is adhered only to the support web 18 and not to the folded panel 14.

Figure 7:
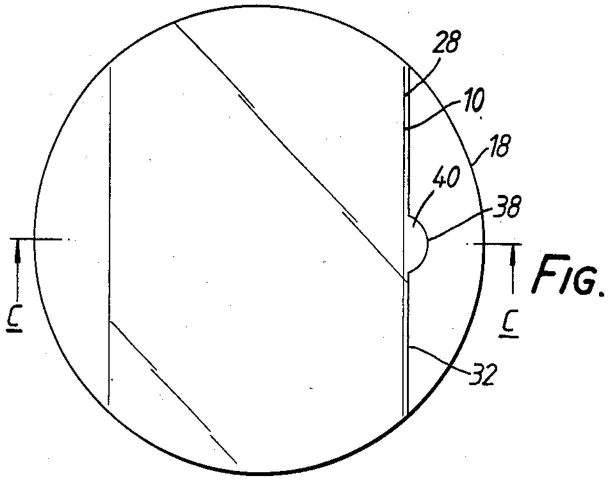
FIG. 7 is a plan view of a label, in a folded condition, in accordance with the third embodiment of the present invention.
Figure 8:
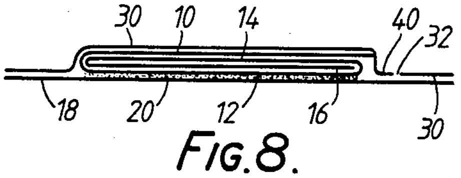
FIG. 8 is a section view, taken along C—C of the label of FIG. 7.

Referring now to FIGS. 7 and 8, in a further alternative arrangement of the label of the present invention the front cover panel 10 is not provided with cut-outs. Instead, in order to provide one or more tabs of plastics material 30 by which the front cover panel 10 is adhered to the support web 18, the cut 32 through the plastics material 30 is not a straight line all along its length, as in the embodiment illustrated in FIGS. 1 to 5. The cut 32 is, however, formed as a line of which a major portion is a straight line extending along the free outer edge 28 of the front cover panel 10 and which is provided with a laterallly extending portion 38 which extends away from the free outer edge 28 of the front cover panel 10. The laterally extending portion 38 defines a tab 40 of plastics material 30 by which the front cover panel 10 is adhered to the support web 18. The folded label may be repeatedly opened and closed by detaching and reattaching the tab 40 from and to the support web 18. In the illustrated embodiment, the tab 40 is semi-circular but it may be made any particular desired shape.

Figure 9:
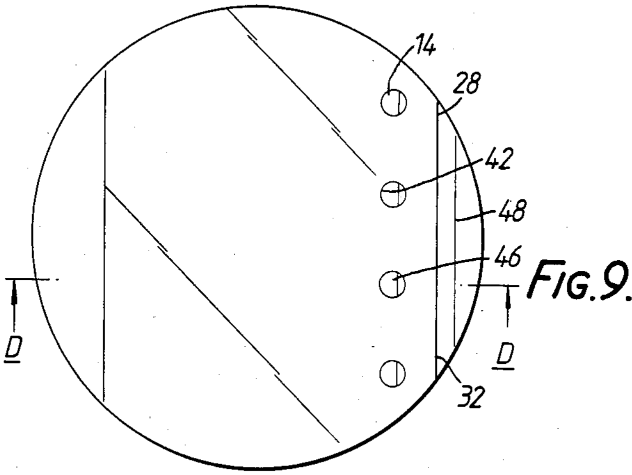
FIG 9 is a plan view of a label, in a folded condition, in accordance with a fourth embodiment of the present invention.
Figure 10:
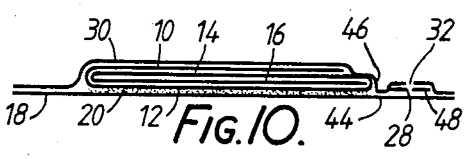
FIG. 10 is a section view, taken along D—D of the label of FIG. 9.

A further embodiment of the label of the present invention is shown in FIGS. 9 and 10. In this embodiment, cut outs 42 are not at the free outer edge 28 of the front cover panel 10 but the cut-outs 42 are punched holes which are situated inwardly of the free outer edge 28 rather than extend inwardly of the free outer edge 28 as in the embodiments of FIGS. 1 to 5 and FIG. 6. In the preferred arrangement which is shown in FIGS. 9 and 10, four circular cut-outs 42 are formed as holes in a line which is parallel to and spaced from the free outer edge 28. The cut-outs 42 are formed by punching or by any other suitable manner. The cut-outs 42 are dimensioned so that when the front cover panel 10 is folded over the remainder of the folded strip, each cut-out 42 reveals an upper portion of the folded panel 14 and also a portion 44 of the support web 18. The layer of plastics material 30 covers the label so that in registry with each cut-out 42 there is a tab portion 46 of the layer of plastics material 30 which is exposed by the respective cut-out 42. When the label is folded as shown in FIGS. 9 and 10, each exposed tab portion 46 of the plastics material 30 is adhered by its self-adhesive surface to the respective revealed portion of folded panel 14 and portion 44 of the support web 18.

Cut 32 is formed as a straight line. However, unlike the previous embodiments the cut 32 passes not only through the layer of plastics material 30 but also the front cover panel 10. Thus cut 32 defines a strip 48 of the edge of front cover panel 10 which is adhered by the layer of plastics material 30 to the support web 18 and is adjacent the foldable part of the front cover panel 10.

In order to open up the folded label and reveal panels 12, 14 and 16 the foldable part of the front cover panel 10 may be pulled open by pulling free outer edge 28 away from the support web 18. The tab portions 46 are released from the folded panel 14 and the portions 44 of the support web 18. After use, the label may be refolded and the tab portions 46 re-adhered by their self-adhesive surface to the folded panel 14 and the portions 44 of the support web 18.

A major advantage of this embodiment of the invention is that by cutting the cut 32 through both the plastics material and front cover panel 10 in a single step the cut edges of the front cover panel 10 and of the plastics material 30 are automatically in registry. In the earlier-described embodiments, the cut 32 is only cut through the plastics material 30 and consequently during the cutting step the cut 32 must be aligned with the free-outer edge 28 of the front cover panel 10, which alignment is often difficult to achieve in a high output automatic production method.

Furthermore, the provision of the punched holes as cut outs 42 is easy to achieve by punching in an automatic production process. The cut-outs 42 permit the front cover panel 10 to be conveniently and satisfactorily adhered along the length of free outer edge 28 to both folded panel 14 and to the support web 18. In this way the front cover panel 10 is firmly adhered to and may readily be re-adhered to the folded panel 14 and to the support web 18.

If desired, the cut-outs 42 may be positioned in the front cover panel 10 such that when the label is folded the tab portions 46 are adhered only to the portions 44 of the support web 18 and not to the folded panel 14.

It will be readily apparent to those skilled in the art that any desired number of tabs 34, 36 or 40 or tab portions 46 may be provided in the labels of the present invention, and that those tab or tab portions may be any appropriate desired shape.

Furthermore, in the above-described embodiments the cut 32 may alternatively be a weakened tear-line, such as, for example, a line of perforations, which is torn when the label is first opened.

In addition, in the embodiments of FIGS. 1 to 5, 6 and 7 and 8 the cut 32 may be spaced from the free outer edge 28 of the front cover panel 10 so as to provide an elongate band of plastics material 30 which can, in addition to the tab or tabs, adhere the front cover panel 10 to the support web 18.

The labels shown in FIGS. 1 to 5, FIGS. 7 and 8 and FIGS. 9 and 10 are circular, with the support web 18 being circular and the folded strip being formed of a plurality of panels each of which has two opposing arc-shaped edges and two opposing straight edges, with adjacent panels being connected via a common straight edge. Of course, it will be readily apparent to those skilled in the art that the labels of the present invention, and the folded strip which is adhered to the support web, may be made any desired shape, such as rectangular as is shown in FIG. 6.

The circular labels of the preferred embodiments have particular application in the labelling of containers which are circular pots or cans having a removable lid, such as paint pots. The labels are dimensioned so that they can be adhered to and fit within the edge of the removable lid. The provision of the layer of plastics material helps to protect the label from accidental damage by tearing or soiling, particularly when the pots are stacked one upon another. The layer of plastics material is see-through and allows information which is printed on the front surface of the label to be seen by a user. The front surface of the folded label may have instructions on how to open the folded label. The surface of the panels of the folded strip, which are revealed when the label is unfolded in the manner described hereinabove, may be printed with information regarding the use of the product in the container or relating to the marketing or promotion of the product.

Figure 11:
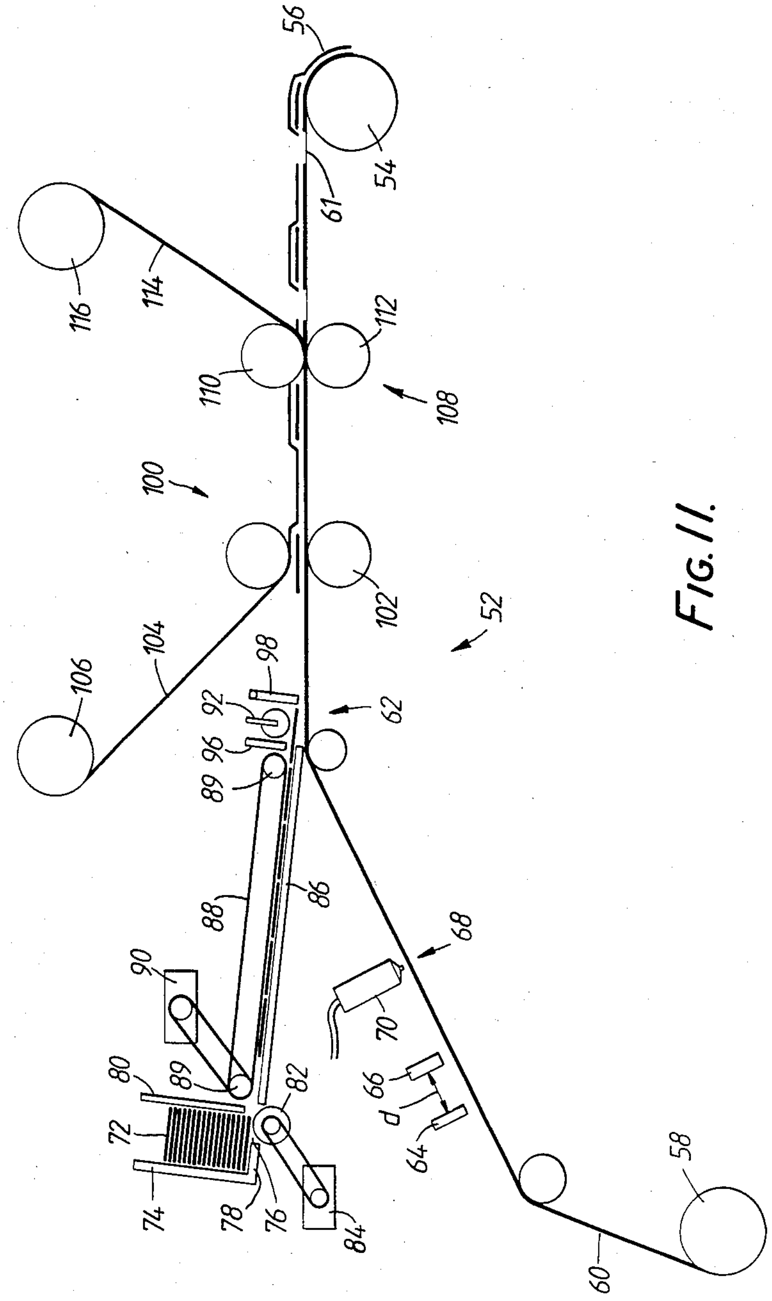
FIG. 11 is a schematic diagram of an apparatus for use in the method of producing labels in accordance with the present invention.

Referring to FIG. 11 there is shown an apparatus, designated generally as 52, for preparing a reel 54 carrying a succession of self-adhesive labels 56 in accordance with the present invention. The reel 54 of labels is produced starting from a reel 58 of a laminar material 60 commonly known in the art as self-adhesive stock or pressure-sensitive stock. Such laminar material usually consists of a support web of paper of indeterminate length coated on its reverse side with a layer of pressure-sensitive adhesive, with the adhesive side of the paper being protected with a backing layer 61 of a release material such as silicone-faced backing paper.

The upper surface of the web of paper is printed along its length with a succession of images, each of which is to constitute the front surface of a respective resultant label 56. Alternatively, the web of paper may not be so printed; such an arrangement is employed when the front surface of the resultant self-adhesive labels 56 is to be composed only of the front surface of the folded longitudinal strip 72 which is adhered to the web of paper in the manner which is described hereinbelow. The folded longitudinal strip 72 is similar to those which are employed in the embodiments of FIGS. 1 to 5, FIG. 6 or FIGS. 7 and 8 or FIGS. 9 and 10.

The laminar material 60 is unwound from the reel 58 and guided by appropriate guide rollers (not shown) to a folded longitudinal strip applying station 62 and passes, in turn, a "START" sensor 64, a "STOP" sensor 66 and an adhesive-applying station 68 including an adhesive applicator 70.

START sensor 64 includes a photodetector which scans the laminar material 60 as its passes thereunder. The photodetector in the START sensor 64 is arranged to detect a mark which is printed at a succession of particular positions along the length of the laminar material 60. When the START sensor 64 detects one of the said marks, an electrical signal is sent therefrom to initiate the operation of the adhesive applicator 70, either immediately or after a predetermined delay of time. The adhesive applicator 70 deposits a layer of adhesive across a particular portion of the width of the laminar material 60. The adhesive may be any suitable adhesive for paper, such as, for example, PVA (poly vinyl alcohol) adhesive. The adhesive is applied to a part of the laminar material 60 which is downstream along the laminar material 60 from that part of the laminar material 60 which was detected by the START sensor 64.

STOP sensor 66 also includes a photodetector which is similar in operation and construction to that included in START sensor 64. The photodetector in STOP sensor 66 detects the same or a different mark on the laminar material 60 as the photodetector in START sensor 64. When the STOP sensor 66 detects the said mark, an electrical signal is sent therefrom to terminate the operation of the adhesive applicator 70, either immediately or after a predetermined delay of time. Thus the laminar material 60 has applied thereto a succession of layers of adhesive of predetermined dimensions. The laminar material 60 is then conveyed to the label applying station 62.

In the preferred arrangement, when the START and STOP sensors 64, 66 detect the same mark the START sensor 64 and the STOP sensor 66 are separated, along the direction of travel of the laminar material 60, by a distance which is equal to the length of each layer of adhesive.

Adhesive applicator 70 may include an applicator head which is elongate and extends transverse the direction of movement of the web. A row of holes is provided along the length of the applicator head. When adhesive is to be applied to the laminar material 60, adhesive is expressed through the holes for a given period on to the upper surface of the moving laminar material 60. This causes a plurality of elongate beads of adhesive of given length to be formed along the length of, and across a desired portion of the width of, the laminar material 60.

In a further arrangement of the adhesive applicator 70, the expressing of the adhesive through the holes may be made intermittent and, in addition, the particular holes through which the adhesive is expressed may be varied for any cycle of adhesive application. The resultant dots of adhesive are deposited on to the laminar material in a manner similar to dot-matrix printing whereby a desired pattern of dots of adhesive is applied to the laminar material 60.

A plurality of the folded longitudinal strips 72 similar to those shown in the preceding figures are held as a stack thereof in a magazine 74. Each folded longitudinal strip 72 is pre-printed as desired and is already formed with the appropriate cut-outs, the type of cut-outs depending on which embodiment of the invention is being made. The front cover panel 10 of the folded strips is the uppermost of the panels of each folded strip so that each folded strip is ready for application to the support web. The bottom of the magazine 74 includes an opening 76 in the bottom wall 78 which extends as far as one of the side walls 80 of the magazine 74. A rotatable cylinder 82 which is hollow and has a plurality of holes provided in the cylindrical wall of the cylinder 82, which holes pass through the thickness of the cylindrical wall, is mounted beneath the opening 76 with the axis of the cylinder being perpendicular to the stack of folded longitudinal strips 72. The cylinder 82 extends into the opening 76 so that the bottom folded strip 72 in the stack rests against the uppermost surface portion of the cylinder 82. A vacuum is continuously maintained in the cylinder 82 by evacuating means (not shown), e.g. a vacuum pump, so that the folded strip 72 which is at the bottom of the stack has the back cover panel 12 thereof which is adjacent the cylinder 82 sucked by the vacuum against the upper surface of the cylinder 82. The strength of the vacuum is such as substantially not to deform the bottom folded strip 72 but so as to ensure that the bottom folded strip 72 can be moved, by rotation of the cylinder 82 by a rotary drove means 84, out of the opening 76 in the magazine 74 against the friction between the said folded strip 72 and the next-to-bottom folded strip 72. The cylinder 82 is rotated intermittently in order successively to feed out folded strips 72 from the stack in the magazine 74. The rotary drive means 84 is preferably an electric motor which drives the cylinder 82 either via a belt or directly.

The folded strips 72 which are fed out from the magazine 74 by the rotation of the vacuum cylinder 82 are deposited onto and travel along the upper surface of a plate 86. The folded strips 72 are conveyed along the plate 86 by means of a rotatable endless belt 88 which is mounted on two spaced rollers 89 and which is driven by a drive means 90 which drives one of the rollers 89. The drive means 90 is an electric motor which drives the roller 89 either via a belt or directly. The endless belt 88 extends along the length of the plate 86 with the bottom surface of the endless belt 88 being located parallel to and slightly above the upper surface of the plate 86 so that each folded strip 72 is held firmly between plate 86 and endless belt 88 as it moves along the plate 86. The endless belt 88 may be made of any suitable material such as, for example, rubber. The endless belt 48 is rotated in an anti-clockwise direction in the apparatus of FIG. 11. The endless belt 88 is rotated intermittently and in synchronism with the rotation of the vacuum cylinder 82, so that when a folded strip 72 is fed out from the magazine 74 by the rotation of the vacuum cylinder 82, the rotating endless belt 88 engages the top surface of the folded strip 72 and urges the folded strip 72 along the plate 86. The duration of the rotation cycle of the vacuum cylinder 82 and the endless belt 48 can be such so as to provide along the plate 86 a succession of folded strips 72 in abutting relationship. Alternatively, the duration of the rotation cycle by be such so as to have the succession of folded strips 72 in overlapping relationship.

A ram 92 for pushing successively the folded strips 72 onto respective layers of adhesive on laminar material 60 as the folded strips 72 reach the downstream end of the plate 86 in turn is mounted slightly spaced from that end of the plate 86.

Preferably the ram 92 consists of one or more rollers. More preferably, the ram 92 consists of one or more rollers which are driven when the ram 92 pushes the folded strips 72 as aforesaid, the speed of rotation of the surface of the rollers being the same as the surface speed of movement of the web.

The folded strip applying station 62 includes control means for controlling the operation of the rotary drive means 84 for the vacuum cylinder 82; control means for controlling the operation of the drive means 90 for the endless belt 88; and the ram 92, and is situated at the downstream end of the plate 86. The label applying station 62 includes a label detector which is a photodetector 96 which is situated at, and directed towards the upper surface of, the downstream end of plate 86. The photodetector 96 detects whether or not a folded strip 72 is underneath the photodetector 96 at the downstream end of the plate 86 by sensing the amount of light reflected into the photodector 96 from the plate 86 or from a folded strip 72. When a folded strip 72 is under the photodetector 96 the amount of light reflected from the folded strip 72 into the photodetector 96 is different from that reflected from the plate 86 when a folded strip 72 is not under the photodetector 96. When the photodetector 96 detects that a folded strip 72 is not under the photodetector 96 at the end of the plate 86, the photodetector 96 emits an electrical signal which switches ON the rotary drive means 84 for the vacuum cylinder 82 and drive means 90 for the endless belt 88. Thus folded strips 72 are fed along the plate 86 from the magazine 74 towards the photodetector 96. The leading folded strip 72 passes along the plate 86 under the photodetector 96 and then under the ram 92.

The leading edge of the leading folded strip 72 then contacts a front-edge detector 98 which is situated downstream of the ram 92 and extends across the pathway of the folded strips 72. The front-edge detector 98 acts as a switch when the front-edge of the leading folded strip 72 contacts the front-edge detector 98. When so contacted, the front-edge detector 98 switches OFF the rotary drive means 84 for the vacuum cylinder 82 and the drive means 90 for the endless belt 88. Thus no more folded strips 72 are fed along the plate 86 when the leading folded strip 72 contacts the front-edge detector which is at the downstream end of the plate 86. The front edge detector 98 also sends an electrical signal to the ram 92 which signal is an ENABLE signal for enabling the ram 92 to operate. The ENABLE signal does not initiate the operation of the ram 92 but rather allows the ram 92 to operate.

The operation of the ram 92 is initiated by an electrical signal which is sent to the ram 92 from START sensor 64. The START sensor 64 sends the signal to the ram 92 when the START sensor 64 initiates the operation of the adhesive applicator 70, either immediately or after a predetermined delay of time. In operation, ram 92 moves downwardly towards and against the upper surface of the leading folded strip 72 so as to push the leading folded strip 72 towards the moving laminar material 60. The arrangement is such that the leading edge of the leading folded strip 72 is pushed by the ram 92 onto a respective adhesive layer on laminar material 60. The ram 92 continues to act on the leading folded strip 72 and the leading folded strip 72 is carried away from the ram 92 by the moving adhesive layer. When the ram 92 consists of one or more undriven rollers, the translational movement of the leading folded strip 72 as it is carried away along the web causes rotation of the one or more rollers. The provision of one or more rollers tends to minimise the frictional resistance acting on the leading folded strips 72 as it moves away from the label applying station 62. When the one or more rollers are driven, the one or more rollers help to overcome the frictional resistance and drive the leading folding strip 72 onto the adhesive layer on the moving web. The ram 92 pushes the leading folded strip 72 beneath the level of the bottom of the front-edge detector 98 so that the adhered folded strip 72 can pass beneath the front-edge detector 98. The ram 92 is arranged to operate when the leading edge of the leading folded strip 72 substantially coincides with the leading edge of the respective layer of adhesive on the laminar material 60. The length of each layer of adhesive substantially corresponds to the length of the back cover of the folded strip 72.

When the folded strip 72 adhered to the laminar material 60 moves away from the label applying station 62, the photodetector 96 senses that there is no folded strip 72 at the end of plate 86 and so initiates the operation of the vacuum cylinder 82 and the endless belt 88 to deliver another folded strip 72 from the magazine 74 onto the upstream end of plate 86 and the new leading folded strip 72 on the plate 86 to the label applying station 62. As the next layer of adhesive passes under the label applying station 62 operation of the ram is initiated as described hereinabove so that the next folded strip 72 is adhered to the next layer of adhesive.

The laminar material 60 with the succession of folded strips 72 applied thereto is then fed to a self-adhesive material applying station 100 which includes a pair of nip rollers 102. At the self-adhesive material applying station 100, an elongate web of a pressure-sensitive self-adhesive material 104, such as a polyester or acetate plastics film having a coating of a pressure-sensitive adhesive, is fed from a reel 106 thereof to the nip rollers 102. The nip rollers 102 press the self-adhesive surface of the self-adhesive material 104 against the upper surface of the laminar material 60 and of the folded strips 72, so that the self-adhesive material 104 is adhered thereto.

The combination of the laminar material 60 with the succession of folded strips 72 applied thereto and the layer of self-adhesive material 104 is then fed to die-cutting station 108 which includes a die-cutting roller 110 coupled with a backing roller 112. At the die-cutting station 108, the die-cutting roller 110 cuts through the self-adhesive material 104, the support web of paper and the folded strips 72 as far as the backing layer 61. The backing layer 61 is not cut by the die-cutting roller, thereby to provide a succession of spaced individual composite labels 56 on the backing layer 61, which is then wound up onto a reel 54. The waste web remnant 114 consisting of portions of the self-adhesive material 104, the web and the folded strips 72 outside the edge of the composite labels 56 is removed from the backing layer 61 and wound up on a roll 116.

When the apparatus is used to manufacture the labels of FIGS. 1 to 5, FIG. 6 or FIGS. 7 and 8, the die-cutting roller 110 also cuts the cut 32 through the layer of self-adhesive material 104 so as to form the tab or tabs of self-adhesive material which releasably adhere the front cover panel 10 of the folded strips 72 to the support web 18.

When the apparatus is used to manufacture the labels of FIGS. 9 and 10, the die-cutting roller also cuts the cut 32 through the layer of plastics material 104 and the front cover panel 10 so that the front cover panel 10 is releasbly adhered to the folded panel 14 and to the support web by the tab portions 46.

If desired, the cut 32 may be cut before or after the cutting of the succession of labels 56 by means of a separate die-cutting roller (not shown)

As is shown in the embodiments of FIGS. 1 to 5, FIG. 6, FIGS. 7 and 8 and FIGS. 9 and 10, in the resultant labels the folded strip may extend across the whole of the width of the support web so that in the cutting step both the support web and the ends of the folded strip are cut away so that the ends of each folded strip coincide with the edge of the support web.

However, if desired, the folded strip may be positioned in the centre of the width of the support web and not be so cut as aforesaid. In such an arrangement, the cut or weakened tear line through the layers of self-adhesive material would have to extend around the sides of the folded strip so as to allow it to be opened by pulling the tab or tabs away from the support web.

What I claim is:

1. A label for affixing to a container comprising a longitudinal strip divided into a series of panels by a plurality of transverse fold lines, the first two panels forming a front cover and a back cover respectively for enveloping the remaining panel or panels of the strip when folded, the transverse fold lines being spaced along the strip so that upon folding of the strip the said remaing panel or panels is or are folded to lie over the back cover and is or are in turn covered by folding of the front cover about the fold line between the front and back covers; a support web to which the said back cover is adhered, the support web being dimensioned so that at least one region thereof extends laterally at least beyond the edge of the back cover which occurs at the fold line between the back cover and the remaining panel or panels; and a layer of pressure-sensitive self-adhesive material which is adhered by the self-adhesive surface thereof over the label, the self-adhesive material extending beyond the free outer edge of the front cover panel, which free outer edge is opposite the fold line between the front and back cover panels, and the self-adhesive material having at least one portion thereof which is releasably adhered by the self-adhesive surface thereof to the at least one region, thereby to secure the front cover panel in a closed condition and can be pulled away from the support web thereby to open the front cover panel and give access to the interior of the folded strip and the self-adhesive material extends beyond the said at least one region so that the self-adhesive material is also adhered to a part of the support web which is adjacent to said at least one region and an elongate cut or weakened tear line through the self-adhesive material separates the said at least one portion from the remainder of the self-adhesive material which is adhered to the said part of the support web.

2. A label according to claim 1 wherein the cut or weakened tear line extends generally along the free outer edge of the front cover panel except at at least one place at which the cut or weakened tear line extends laterally away from the free outer edge to form the said at least one portion of self-adhesive material.

3. A label according to claim 2 wherein the front cover panel is dimensioned so that the free outer edge extends beyond the area of the support web occupied by the back cover thereby to form an overlapping portion, the overlapping portion being provided with at least one cut-out which exposes the self adhesive surface of the self-adhesive material so as to form the said at least one portion of self-adhesive material.

4. A label according to claim 3, wherein the or each cut-out extends inwardly from the free outer edge to a distance which is greater than the width of the overlapping portion so that the or each portion of self-adhesive material can be adhered both to the support web and to the upper surface of the remaining panel or panels which are exposed by the or each cut-out.

5. A label according to claim 3, wherein the free outer edge of the front cover panel is, apart from the cut outs, a straight line and the cut or weakened tear line is a straight line which is coincident with the straight line of the free outer edge.

6. A label according to claim 2, wherein the free outer edge of the front cover panel is a straight line and the cut or weakened tear line is substantially a straight line except at the said at least one place.

7. A label for affixing to a container comprising a longitudinal strip divided into a series of panels by a plurality of transverse fold lines, the first two panels forming a front cover and a back cover respectively for enveloping the remaining panel or panels of the strip when folded, the transverse fold lines being spaced along the strip so that upon folding of the strip the said remaining panel or panels is or are folded to lie over the back cover and is or are in turn covered by folding of the front cover about the fold line between the front and back covers; a support web to which the said back cover is adhered, the support web being dimensioned so that at least one region thereof extends laterally at least beyond the edge of the back cover which occurs at the fold line between the back cover and the remaining panel or panels; and a layer of pressure-sensitive self-adhesive material which is adhered by the self-adhesive surface thereof over the label, the self-adhesive material extending beyond the free outer edge of the front cover panel, which free outer edge is opposite the fold line between the front and back cover panels, and the self-adhesive material having at least one portion thereof which is releasaby adhered by the self-adhesive surface thereof to the at least one region, thereby to secure the front cover panel in a closed condition and can be pulled away from the support web thereby to open the front cover panel and give access to the interior of the folded strip, the self-adhesive material extending beyond the said at least one region so that the self-adhesive material is also adhered to a part of the support web which is adjacent to said at least one region and an elongate cut or weakened tear line through the self-adhesive material separates the said at least one portion from the remainder of the self-adhesive material which is adhered to the said part of the support web; and the front cover panel is dimensioned so that the free outer edge extends beyond the area of the support web occupied by the back cover thereby to form an overlapping portion, the overlapping portion being provided with two or more cut-out holes which are spaced from and generally along the free outer edge of the front cover panel, each cut-out hold exposing the self-adhesive material so as to form two or more of the said portions of self-adhesive material.

8. A label according to claim 7, wherein each cut-out hole is positioned in the front cover panel such that when tne front cover panel is folded over the remaining panel or panels each portion of self-adhesive material can be adhered both to the support web and to the upper surface of the remaining panel or panels which are exposed by the respective cut-out holes.

9. A label according to claim 7 further comprising a band of the material of the longitudinal strip which is disposed along the free outer edge of the front cover panel when the front cover panel is folded as aforesaid, the band being separated from the front cover panel by the cut or weakened tear line and being adhered to the support web by the remainder of the self-adhesive material which is adhered to the support web.

10. A reel of release backing carrying thereon a succession of labels as claimed in any of claims 1 or 3-10.

* * * * *